United States Patent
Garvey et al.

(10) Patent No.: US 6,217,707 B1
(45) Date of Patent: Apr. 17, 2001

(54) CONTROLLED COVERAGE ADDITIVE APPLICATION

(75) Inventors: Lee Patrick Garvey, Little Chute; Robert Timothy Drozd, Appleton; Cynthia Watts Henderson, Neenah; Marc David Couture, Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/994,603

(22) Filed: Dec. 19, 1997

Related U.S. Application Data

(60) Provisional application No. 60/034,838, filed on Dec. 31, 1996.

(51) Int. Cl.[7] .................................................. D21H 23/22
(52) U.S. Cl. ........................ 162/109; 162/134; 162/135; 162/158; 162/184
(58) Field of Search ..................... 162/109, 111, 162/112, 134, 135, 137, 158, 184; 427/288, 395

(56) References Cited

U.S. PATENT DOCUMENTS

| | | | |
|---|---|---|---|
| 1,102,203 | 6/1914 | Scott . | |
| 1,775,998 | 9/1930 | Greenberg . | |
| 1,960,192 | 5/1934 | Howard | 15/209 |
| 2,288,714 | 7/1942 | Jones | 15/209 |
| 2,785,083 | 3/1957 | Robinson | 117/44 |
| 2,860,068 | 11/1958 | Griswold | 117/38 |
| 2,904,448 | 9/1959 | Sorg | 117/38 |
| 3,009,822 | 11/1961 | Drelich et al. | 117/38 |
| 3,025,829 | 3/1962 | Smith | 118/221 |
| 3,106,481 | 10/1963 | Sorg | 117/44 |
| 3,264,188 | 8/1966 | Gresham | 167/84 |
| 3,299,852 | 1/1967 | Seeley | 118/68 |

(List continued on next page.)

FOREIGN PATENT DOCUMENTS

| | | | |
|---|---|---|---|
| 977197 | 11/1975 | (CA) . | |
| 1304996 | 7/1992 | (CA) . | |
| 0 033 988 A2 | 8/1981 | (EP) | D21D/3/00 |
| 1127438 | 9/1968 | (GB) | A44K/15/00 |
| WO 94/29524 A1 | 12/1994 | (WO) | D21H/23/58 |
| WO 95/16824 A1 | 6/1995 | (WO) | D21H/17/14 |
| WO 95/23009 A1 | 8/1995 | (WO) | A61M/35/00 |
| WO 95/35411 A1 | 12/1995 | (WO) | D21H/21/24 |
| WO 95/35412 A1 | 12/1995 | (WO) | D21H/21/24 |
| WO 96/24722 A1 | 8/1996 | (WO) | D21H/19/18 |
| WO 96/24723 A1 | 8/1996 | (WO) | D21H/19/18 |

* cited by examiner

*Primary Examiner*—Peter Chin
(74) *Attorney, Agent, or Firm*—Thomas M. Gage; Patricia A. Charlier

(57) ABSTRACT

A soft tissue product includes deposits of a surface additive composition disposed in primary and supplementary delivery zones having different add-on levels. The supplementary add-on level is greater than 0 and less than the primary add-on level. For example, the supplementary add-on level may be from about 0.5 to about 80 percent of the primary add-on level. In particular embodiments, the primary delivery zones cover from about 30 to about 90 percent of the tissue and the supplementary delivery zones cover from about 10 to about 70 percent of the tissue. The different add-on levels effectively maximize consumer benefit while minimizing the total amount of additive on the tissue.

31 Claims, 5 Drawing Sheets

U.S. PATENT DOCUMENTS

| | | | |
|---|---|---|---|
| 3,305,392 | 2/1967 | Britt | 117/154 |
| 3,363,604 | 1/1968 | Pschibul | 118/212 |
| 3,416,943 | 12/1968 | Clark et al. | 117/44 |
| 3,769,060 | 10/1973 | Ida et al. | 117/37 R |
| 3,791,266 | 2/1974 | Bucalo | 93/1 R |
| 3,798,120 | 3/1974 | Enloe et al. | 162/112 |
| 3,818,533 | 6/1974 | Scheuer | 15/104.93 |
| 3,846,158 | 11/1974 | Vasilyadis | 117/68.5 |
| 3,896,807 | 7/1975 | Buchalter | 128/261 |
| 3,965,817 | 6/1976 | Ipek | 101/120 |
| 4,094,241 | 6/1978 | Kossler | 101/120 |
| 4,106,433 | 8/1978 | Fernando et al. | 118/212 |
| 4,161,422 | 7/1979 | Lawson et al. | 162/135 |
| 4,239,591 | 12/1980 | Blake | 162/109 |
| 4,426,418 | 1/1984 | Coleman et al. | 428/211 |
| 4,447,294 | 5/1984 | Osborn, III | 162/158 |
| 4,481,243 | 11/1984 | Allen | 428/154 |
| 4,507,173 * | 3/1985 | Klowak et al. | 162/112 |
| 4,513,051 | 4/1985 | Lavash | 428/212 |
| 4,528,239 | 7/1985 | Trokhan | 428/247 |
| 4,561,354 | 12/1985 | Glantschnig et al. | 101/120 |
| 4,601,938 | 7/1986 | Deacon et al. | 428/153 |
| 4,610,743 * | 9/1986 | Salmeen et al. | 162/112 |
| 4,681,780 | 7/1987 | Kamman | 427/282 |
| 4,702,943 | 10/1987 | Long | 427/282 |
| 4,740,391 | 4/1988 | Long | 427/286 |
| 4,747,365 | 5/1988 | Tusch | 118/221 |
| 4,786,367 | 11/1988 | Bogart et al. | 162/158 |
| 4,814,204 | 3/1989 | Carey et al. | 427/286 |
| 4,849,261 | 7/1989 | Long | 427/282 |
| 4,883,475 | 11/1989 | Bogart et al. | 604/290 |
| 4,943,350 | 7/1990 | Bogart et al. | 162/158 |
| 4,950,545 | 8/1990 | Walter et al. | 428/446 |
| 4,955,298 | 9/1990 | Zimmer et al. | 101/120 |
| 4,976,961 | 12/1990 | Norbury et al. | 424/401 |
| 4,987,632 | 1/1991 | Rowe et al. | 15/104.93 |
| 5,141,803 | 8/1992 | Pregozen | 428/288 |
| 5,152,996 | 10/1992 | Corey et al. | 424/443 |
| 5,183,691 | 2/1993 | Hassell et al. | 427/286 |
| 5,209,953 | 5/1993 | Grupe et al. | 427/276 |
| 5,215,626 | 6/1993 | Ampulski et al. | 162/112 |
| 5,227,242 | 7/1993 | Walter et al. | 428/446 |
| 5,239,922 | 8/1993 | Zimmer | 101/120 |
| 5,246,545 | 9/1993 | Ampulski et al. | 162/112 |
| 5,246,546 | 9/1993 | Ampulski | 162/112 |
| 5,255,603 | 10/1993 | Sonneville et al. | 101/363 |
| 5,354,425 | 10/1994 | Mackey et al. | 162/135 |
| 5,362,488 | 11/1994 | Sibley et al. | 424/78.05 |
| 5,387,284 | 2/1995 | Moody | 118/220 |
| 5,409,747 | 4/1995 | Pearlstein et al. | 428/34.2 |
| 5,419,912 | 5/1995 | Morimoto et al. | 424/443 |
| 5,436,007 | 7/1995 | Hartung et al. | 424/402 |
| 5,446,114 | 8/1995 | O'Lenick, Jr. | 528/15 |
| 5,494,731 | 2/1996 | Fereshtehkhou et al. | 428/211 |
| 5,525,345 | 6/1996 | Warner et al. | 424/402 |
| 5,525,346 | 6/1996 | Hartung et al. | 424/402 |
| 5,527,560 | 6/1996 | Fereshtehkhou et al. | 427/288 |
| 5,558,873 | 9/1996 | Funk et al. | 424/401 |
| 5,573,637 | 11/1996 | Ampulski et al. | 162/112 |
| 5,601,871 | 2/1997 | Krzysik et al. | 427/288 |
| 5,607,551 | 3/1997 | Farrington, Jr. et al. | 162/109 |
| 5,614,293 | 3/1997 | Krzysik et al. | 428/211 |
| 5,624,676 | 4/1997 | Mackey et al. | 424/414 |
| 5,650,218 | 7/1997 | Krzysik et al. | 428/195 |
| 5,665,426 | 9/1997 | Krzysik et al. | 427/211 |
| B1 3,814,096 | 10/1988 | Weiss et al. | 604/289 |

CONTROLLED COVERAGE ADDITIVE APPLICATION

This application claims priority from U.S. Provisionsl Application No. 60/034,838 filed on Dec. 31, 1996.

BACKGROUND OF THE INVENTION

Absorbent tissue products such as facial tissue and bath tissue have been used to absorb body fluids and leave the skin dry. Frequent use of absorbent tissues may, however, tend to abrade the skin. In particular, during frequent nose-blowing, the skin can become so abraded as to appear red and be sore to the touch. To reduce skin abrasion, tissue products have included additives applied to the tissue surfaces to reduce or eliminate abraded skin during heavy use periods. The additives can enhance sheet softness perceptions by reducing the stiffness of the sheet, making it more drapeable, or by providing lubricity, helping the sheet glide across the surface of the skin. The additives may also be deposited on the skin.

Until now, the general approach in the industry has been that the greater the quantity of additive on the tissue, the greater the benefit. Contributing to this approach is the fact that particular additives may be absorbed into the tissue, leaving less additive on the surface to provide the intended benefit.

One major drawback to the "more is better" philosophy is cost. Additives to address skin abrasion can represent a significant portion of the cost of a tissue sheet. Also, for some additives, relatively high addition levels can be difficult to manufacture.

Thus, there is a need for a tissue product including an additive adapted to enhance sheet softness and/or reduce skin irritation and redness, where the additive is present at an economical, yet effective, add-on amount. There is also a need for a cost effective method to manufacture a tissue product including such an additive.

SUMMARY OF THE INVENTION

It has now been discovered that, surprisingly, tissue products containing an additive adapted to reduce skin irritation and redness can be manufactured with substantially lower total add-on amounts without decreasing the effectiveness of the additive. Applicants have discovered that an array of primary delivery zones with a relatively high additive add-on amount in combination with supplementary delivery zones with a relatively lower add-on amount can be used effectively to maximize consumer benefit while minimizing the total amount of additive on the tissue.

In one embodiment, a tissue product defines a major surface having a planar surface area. The tissue product comprises an additive composition disposed on the major surface in at least one primary delivery zone and at least one supplementary delivery zone. The primary delivery zone has a primary add-on level and the supplementary delivery zone has a supplementary add-on level. The supplementary add-on level is greater than zero and from about 0.5 to about 80 percent of the primary add-on level.

In another embodiment, a tissue product comprises an additive composition disposed on a major surface in at least one primary delivery zone having a primary add-on level and at least one supplementary delivery zone having a supplementary add-on level. The supplementary add-on level is greater than zero and the primary add-on level is greater than the supplementary add-on level. The primary delivery zone covers from about 30 to about 90 percent of the tissue surface area and the supplementary delivery zone covers from about 10 to about 70 percent of the tissue surface area.

The primary and supplementary add-on amounts, and the number, size, shape, and position of the primary and supplementary delivery zones, can be selected to maximize the overall benefit provided to the consumer while minimizing the total add-on amount. The terms "primary add-on amount" and "primary add-on level" refer to the basis weight of additive composition in the primary delivery zone or zones, typically measured in grams per square meter (gsm). In contrast, the terms "supplementary add-on amount" and "supplementary add-on level" refer interchangeably to the basis weight of additive composition in the supplementary delivery zone or zones. Thus, for any given tissue including a surface additive composition segmented into zones having different add-on amounts, the zone or zones having higher add-on amounts are deemed the primary delivery zones and the zone or zones having lower add-on amounts are deemed the supplementary delivery zones. The primary and supplementary delivery zones may be used on one or both surfaces of the tissue.

For purposes of the present invention, the primary add-on amount is generally set as the level of the selected additive that provides a high degree of satisfaction on the part of the consumer. The supplementary add-on amount provides a lesser degree of consumer satisfaction than the primary add-on amount, but significantly, it still provides some degree of benefit. The actual basis weight values for the primary and supplementary add-on amounts may need to be determined by comparing the consumer benefits obtained from a series of test tissue products that differ from one another only in the additive add-on amount, each having a uniform application of the additive deposited on one surface or both surfaces. The primary add-on amount will be the same as or similar to the add-on amount on the test tissue products that deliver the desired level of consumer benefit. The supplementary add-on amount will then be greater than zero but less than the primary add-on amount.

The number, size, shape and position of the primary delivery zone or zones on a particular tissue are selected so as to obtain the same or substantially the same consumer benefit as would be obtainable from a tissue having a uniform add-on amount equal to the primary add-on amount. One or more supplementary delivery zones are provided on the tissue product so as not to detract from the benefit delivered by the primary delivery zones. The supplementary delivery zones allow for a reduction in the cost of the tissue product compared to what would result if the total coverage area included the additive composition at the primary add-on amount. It is theorized that "additive void areas," that is, areas on the surface of the tissue that do not contain the additive composition, significantly detract from the benefit provided by the primary delivery zone or zones. The combination of primary and supplementary delivery zones is thought to allow delivery of the consumer benefit afforded by the primary add-on amount but at a lower cost.

By way of illustration, a single primary delivery zone may be centrally located on the tissue surface and comprise about 65 percent of the planar surface area of the tissue. A single supplementary delivery zone may completely surround the primary delivery zone and comprise about 35 percent of the planar surface area. In this embodiment, the primary delivery zone is centrally located to maximize the opportunity for the higher, primary add-on amount of additive to contact the skin during product use to yield maximum benefit. The supplementary delivery zone provides some benefit, and importantly does not detract from the benefit derived from the primary delivery zone. Such a tissue is believed to be capable of providing consumer benefits comparable to a tissue having a uniform additive add-on amount equal to the primary add-on amount centrally located over 100 percent of the planar surface area, and at a reduced cost.

By way of further illustration, the tissue product may comprise an alternating pattern of primary and supplementary delivery zones. This product as well is capable of providing the consumer benefits associated exclusively with the higher add-on amount, but at a reduced cost because the primary delivery zones tend to mask the reduction in additive of the supplementary delivery zones. Again, the placement of the supplementary delivery zones adjacent the primary delivery zones does not reduce the benefits delivered by the primary delivery zones, as would otherwise be the case if additive void areas took the place of the supplementary delivery zones.

It should be readily appreciated that a wide variety of configurations of the number, size, shape, and position of the primary and supplementary delivery zones may be possible. The specific size of the primary delivery zones and the supplementary delivery zones will depend upon the desired effect of the composition and the specific composition.

For example, in the course of blowing or wiping the nose, pressure is exerted against the tissue and nose by the fingers. Therefore the size of the zones can be regulated by the dimension of a single finger or several fingers used jointly to apply pressure while wiping the nose. Ideally the additive regions giving the most important benefit, that is the primary delivery zones, would each have an individual zone size at least as large as those dimensions so that at any one point of contact during wiping the most important additive is always in contact with the skin. Furthermore, each individual supplementary delivery zone would preferably have an individual zone size smaller than that of the primary delivery zones and thus smaller than the dimension of a single finger or several fingers. When using primary and supplementary delivery zones, limited use of additive void areas may be acceptable. Desirably, of course, the dimension of additive void areas, if incorporated into the design, would be even further reduced.

Using this as an example, a single primary delivery zone may desirably have a width dimension of from about 0.2 inch to about 5.5 inches, such as about 0.2 to about 4 inches, more specifically from about 0.4 inch to about 2 inches, and still more specifically from about 0.5 inch to about 1.5 inches. A single supplementary delivery zone may desirably have a width dimension of from about 0.1 inch to about 2 inches, more specifically from about 0.2 inch to about 1 inch, and still more specifically from about 0.25 to about 0.75 inch. If present at all, each additive void area will desirably have a width dimension of from about 0.003 inch to about 1 inch, more specifically from about 0.008 inch to about 0.5 inch, and still more specifically from about 0.02 inch to about 0.2 inch. It should be appreciated that there might be conditions such as cost, wiping task, and the like that would change these primary, supplementary, and void area zone size relationships. The length dimensions of the primary and supplementary delivery zones and the additive void areas may extend over the entire tissue or only over part of the tissue.

It is generally thought to be desirable for the primary and supplementary delivery zones to be positioned immediately adjacent one another. As used herein, the term "immediately adjacent" refers to the primary and supplementary delivery zones having at least one common boundary, rather than being separated by an additive void zone. It is hypothesized that the effectiveness of the additive composition in the primary delivery zones is maintained to a greater extent when the primary delivery zones are disposed adjacent supplementary delivery zones as opposed to adjacent additive void zones.

The specific area coverage of the primary delivery zones, the supplementary delivery zones, and the void areas will depend upon the desired effect of the composition and the specific composition. The tissue coverage of the primary zones will generally be from about 30 to about 90 percent, more specifically from about 40 to about 80 percent, and more specifically from about 50 to about 75 percent, based on the simple planar view surface area of the tissue. The tissue coverage of the supplementary zones will generally be from about 10 to about 70 percent, more specifically from about 20 to about 60 percent, and more specifically from about 25 to about 50. The void areas that may be present will generally represent from about 0.5 to about 50 percent, more specifically from about 1 to about 25 percent, and still more specifically from about 1 to about 12 percent. Correspondingly, the primary and supplementary delivery zones desirably have a combined surface area of at least about 50 percent, more particularly at least about 75 percent, and even more particularly at least about 88 percent, such as 100 percent, of the planar surface area. The total tissue area coverage of the primary delivery zones, supplementary delivery zones, and the void areas represent, by definition, 100 percent of the tissue surface area, based on the simple planar view surface area.

Another aspect of the invention relates to a method of making a tissue product. The method comprises the steps of: providing a tissue web and an additive composition; applying the additive composition to the tissue web using a rotogravure process comprising an engraved roll having primary and supplementary regions, the primary and supplementary regions adapted to provide different add-on rates; and recovering from the rotogravure process a tissue product having the additive composition disposed in both a primary delivery zone having a primary add-on level and a supplementary delivery zone having a supplementary add-on level, with the supplementary add-on level being greater than zero and from about 0.5 to about 80 percent of the primary add-on level.

One particularly beneficial method is to uniformly apply the composition to the surface of the tissue web within each of the zones by rotogravure printing, either direct or indirect (offset), because it is a very exact printing process and offers maximum control of the composition distribution and transfer rate. However, other application methods, such as flexographic printing, spraying, extruding, and the like can also be used.

Typical of gravure printing, the additive composition in each of the primary and supplementary delivery zones may actually be present in a large number of small, spaced apart deposits on the tissue surface. These deposits are desirably uniformly positioned within each zone but only cover part of the surface in each zone. When viewed by the naked eye, the large number of small spaced-apart deposits appear to cover the entire surface, but in fact do not. The actual surface area coverage of the deposits can be from about 30 to about 99 percent, more specifically from about 50 to about 80 percent. For purposes of the present invention, the surface areas of the primary and supplementary delivery zones include the complete area circumscribed by the pattern of deposits, and not just the actual surface area coverage of the deposits.

Gravure printing is ideally suited to such an application by providing, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. Gravure printing encompasses several well known engraving techniques, such as mechanical engraving, acid-etch engraving, electronic engraving and ceramic laser engraving. A suitable electronic engraved example for a primary delivery zone is about 200 deposits per lineal inch of surface, or about 40,000 deposits per square inch. By providing such a large number of small deposits, the uniformity of the deposit distribution is very high. Also, because of the large number of small deposits applied to the surface of the tissue, the deposits more readily resolidify on the surface of the tissue where they are most effective in benefiting the user. As a consequence, a relatively low amount of the composition can be used to cover a large area.

The add-on rate is also determined by the volume of the gravure roll engraving. Typically, this is expressed in terms of the volume of the cells per square inch of engraved area. The volume in the primary delivery regions will deliver more additive composition than the volume in the supplementary delivery regions. The range of liquid cell volume for a primary delivery region, described in terms of cubic billion microns (CBM) per square inch, is suitably from about 0.5 to about 15 CBM per square inch, more specifically from about 1 to about 10 CBM per square inch, and still more specifically from about 1.5 to about 8 CBM per square inch. The range of liquid cell volume for a supplementary delivery region is suitably from 0.1 to about 10 CBM per square inch, more specifically from about 0.5 to about 8 CBM per square inch, and still more specifically from about 0.75 to about 6 CBM per square inch.

The additive composition or compositions can be applied to one or both outer surfaces of a tissue. The additive composition can be waterbased or oil-based. Suitable water-based compositions include, but are not limited to, emulsions and water-dispersible compositions which can contain, for example, debonders (cationic, anionic or nonionic surfactants), or polyhdroxy compounds such as glycerin or propylene glycol. The basesheet could be treated with a bi-component system comprising a debonder and a polyhydroxy compound. Both components can be added separately or mixed together prior to being applied to the basesheet. In particular embodiments, the primary and supplementary delivery zones or the opposite sides of the tissue could comprise different additive compositions.

In particular embodiments, the tissue products are made by applying, on the surface(s) of the tissue, large numbers of individual deposits of a melted moisturizing/protective additive composition comprising a wax and an oil, and thereafter resolidifying the composition to form a distribution, of solid deposits on the surface(s) of the tissue. Because the composition is a solid at room temperature and rapidly solidifies after deposition, it has less tendency to penetrate and migrate into the sheet. Compared to tissues treated with liquid formulations, this leaves a greater percentage of the added composition on the surface of the tissue where it can contact and/or transfer to the user's skin to provide a benefit. Furthermore, a lower add-on amount can be used in both the primary and supplementary zones to deliver the same benefit at lower cost because of the efficient placement of the composition substantially at the surface of the product.

The additive composition may comprise solidified deposits of a composition comprising from about 30 to about 90 weight percent oil, and from about 10 to about 40 weight percent wax, preferably also containing from about 5 to about 40 weight percent fatty alcohol, said composition having a melting point of from about 30° C. to about 70° C., more specifically from about 40° C. to about 60° C. For purposes herein, "melting point" is the temperature at which the majority of the melting occurs, it being recognized that melting actually occurs over a range of temperatures.

The amount of oil in the composition can be from about 30 to about 90 weight percent, more specifically from about 40 to about 70 weight percent, and still more specifically from about 45 to about 60 weight percent. Suitable oils include, but are not limited to, the following classes of oils: petroleum or mineral oils, such as mineral oil and petrolatum; animal oils, such as mink oil and lanolin oil; plant oils, such as aloe extract, sunflower oil and avocado oil; and silicone oils, such as dimethicone and alkyl methyl silicones.

The amount of wax in the composition can be from about 10 to about 40 weight percent, more specifically from about 10 to about 30 weight percent, and still more specifically from about 15 to about 25 weight percent. Suitable waxes include, but are not limited to the following classes: natural waxes, such as beeswax and carnauba wax; petroleum waxes, such as paraffin and ceresine wax; silicone waxes, such as alkyl methyl siloxanes; or synthetic waxes, such as synthetic beeswax and synthetic sperm wax.

The amount of fatty alcohol in the composition, if present, can be from about 5 to about 40 weight percent, and more specifically from about 10 to about 30 weight percent. Suitable fatty alcohols include alcohols having a carbon chain length of $C_{14}$–$C_{30}$, including acetyl alcohol, stearyl alcohol, behenyl alcohol, and dodecyl alcohol.

In order to better enhance the benefits to consumers, additional ingredients can be used. The classes of ingredients and their corresponding benefits include, without limitation, $C_{10}$ or greater fatty alcohols (lubricity, body, opacity); fatty esters (lubricity, feel modification); vitamins (topical medicinal benefits); dimethicone (skin protection); powders (lubricity, oil absorption, skin protection); preservatives and antioxidants (product integrity); ethoxylated fatty alcohols; (wetability, process aids); fragrance (consumer appeal); lanolin derivatives (skin moisturization), colorants, optical brighteners, sunscreens, alpha hydroxy acids, natural herbal extracts, and the like.

The above additive composition may be applied to one or both outer surfaces of the tissue by heating the composition to a temperature above the melting point of the composition, for instance a melting point of from about 30° C. to about 70° C., thereby causing the composition to melt. The additive is then uniformly applied within each of the primary and supplementary zones at the predetermined add-on amounts for such zones by uniformly applying the melted composition to one or both surfaces of a tissue web in spaced-apart deposits. Thereafter, the deposits of the melted composition are resolidified. Resolidification of the deposits can occur almost instantaneously, without the need for external cooling means such as chill rolls, if the composition is heated to a temperature only slightly above or at the melting point of the composition. However, external cooling means such as chill rolls, either before or after the application of the melt, can be used if desired to accelerate resolidification. Such instantaneous resolidification tends to impede penetration of the composition into the tissue and retain it on the surface of the tissue, which is advantageous. For example, the temperature of the melted composition can advantageously be above the melting point about 10° C. or less, more specifically about 5° C. or less, and still more specifically about 2° C. or less. As the temperature of the melted composition approaches the melting point, the viscosity of the melted composition generally increases, which further enhances the tendency of the melted composition to be retained on the surface.

Surface additive compositions of the foregoing type comprising a wax and an oil are disclosed in International Patent Application PCT/US96/01243 published Aug. 15, 1996 and identified as WO 96/24722; and International Patent Application PCT/US96/01297 published Aug. 15, 1996 and identified as WO 96/24723; the disclosures of which are incorporated herein by reference.

The total tissue add-on amount of the additive composition represents the combined primary and supplementary add-on amounts and can be from about 1 to about 40 weight percent, more specifically from about 3 to about 15 weight percent, and still more specifically from about 5 to about 10 weight percent, based on the weight of the tissue. The add-on amount for each of the primary and supplementary delivery zones will depend upon the desired effect of the composition on the product attributes and the specific composition. Generally, though, with respect to an additive composition of the foregoing type comprising a wax and an oil, the primary add-on amount is suitably from about 1 to about 35 weight percent, more specifically from about 3 to about 15 weight percent, and still more specifically from about 4 to about 10 weight percent, based on the weight of the tissue. Moreover, the supplementary add-on amount is suitably from about 0.2 to about 28 weight percent, more specifically from about 0.5 to about 12 weight percent, and still more specifically from about 1 to about 8 weight percent, based on the weight of the tissue. Relative to one another, the supplementary add-on amount for an additive composition comprising a wax and an oil is preferably from about 0.5 to about 80 percent, more specifically from about 5 to about 70, and still more specifically from about 15 to about 50 percent, of the primary add-on amount.

The presence of the additive composition comprising a wax and an oil and the differences in add-on amounts in the various zones of the tissue, can be verified by image analysis of the surface or surfaces of the tissue after treatment with osmium tetroxide to stain the add-on composition. The uniformity of the osmium-stained tissues within each of the primary and supplementary delivery zones can be characterized by a percent coefficient of variation of about 15 or less, more specifically about 10 or less, and still more specifically from about 5 to about 15. The degree of penetration (or lack of penetration) of the osmium-stained composition can be characterized by a mean gray level difference between opposite sides of a single ply of the tissue, $GL_{DIFF}$ (hereinafter defined), of about 5 or greater, more specifically about 10 or greater, and still more specifically from about 5 to about 15.

The osmium tetroxide staining treatment used to measure the uniformity and the penetration of the composition is carried out by placing the tissues loosely in a glass bell jar having an opening diameter of about 12–16 inches and a depth of about 12 inches. Care is taken not to stack the tissues, which would hinder adequate penetration of the vapors to all tissues. Osmium tetroxide is received as a crystalline solid in a sealed glass ampule which is broken open and placed in the bell jar with the tissues. The top is placed on the bell jar forming an air-tight seal. The tissues remain in the bell jar for about 24 to 48 hours. The osmium tetroxide has a high vapor pressure and sublimes readily to a gas which permeates the bell jar chamber. After staining is complete, the bell jar is opened and the samples are allowed to ventilate 12 to 24 hours before handling in order to release any residual unreacted vapors. Note: the greatest care must be exercised when using osmium tetroxide. It is a powerful oxidizer and highly toxic. All procedures with this material should be conducted in a fume hood with adequate air flow.

In order to measure the percent coefficient of variation, the osmium-treated sheet is viewed with an omnidirectional darkfield lighting produced by an 8-bulb octagonal ring illuminator surrounding a 50 millimeter EL-Nikkor lens attached to a 10 millimeter C-mount extension tube. This is input into a Quantimet 970 Image Analysis System (Leica, Deerfield, Ill.) by a chalnicon scanner. The field size (standard live frame) is 2.77 centimeter×2.17 centimeters, or adjusted to be smaller to accommodate narrower shaped primary or secondary zones. Various fields of the osmium-treated tissue sample are placed under the lens and measured using a black photodrape background. Six (6) fields in total are measured. The scanner white level is always set at 1.00 volt. At the end, the histogram is printed out and its standard deviation divided by its mean gray level is the coefficient of variation. When multiplied by 100, this becomes the percent coefficient of variation.

In order to determine the mean gray level difference, the imaging and optical conditions used are the same as described above for the uniformity measurement. But in this case, top surface and bottom surface pieces of each ply of tissue are placed tightly next to each other to from a "butt joint" with no gap between the two pieces. The sample is placed under the lens with, for example, the lighter bottom surface piece on the right of the image frame and the darker top surface piece on the left of the image frame.

If first measuring the gray-level histogram of the lighter, bottom surface, the variable live frame is placed over just that region of the image frame, with the scanner white level set at 1.00 volt for the whole field. Then the sample is rotated so that the lighter bottom surface is now on the left. The scanner is adjusted against to 1.00 volt and this surface is once again isolated by the variable live frame. This data is accumulated into the same gray-level histogram. The mean gray level of the bottom surface, $GL_{BOTTOM}$, is recorded.

The same procedure is then conducted on the darker, top surface that occupies the other half of the image, again with the scanner white level set at 1.00 volt for the entire image. This will tend to compensate for the overall difference in the amount of the composition added to the tissue, while zeroing in more accurately on whether the composition is on the top or bottom surface, which reflects the degree of penetration. Again, the mean gray level of the top surface, $GL_{TOP}$, is recorded.

Finally, the difference between the two mean gray levels, $GL_{DIFF}$, is calculated as a value inversely related to the penetration:

$$GL_{DIFF}=GL_{BOTTOM}-GL_{TOP}$$

Note that if $GL_{DIFF}$ is zero or negative, then complete penetration has occurred. If $GL_{DIFF}$ is strongly positive, then most of the osmium-stained composition is sitting on the top surface of the tissue.

The additive composition may alternatively comprise a silicone compound. Suitable silicone compounds are those silicone compounds which provide a smooth, lubricated surface feel, preferably without smearing glass. Preferably the silicone compounds are present in an aqueous emulsion and/or solution for ease in handling and processing. A wide variety of such silicone compounds are known in the art.

Specific suitable silicone compositions include, without limitation, polydimethyl siloxanes; mixtures of polydimethyl siloxanes and alkylene oxide-modified polydimethyl siloxanes; organomodified polysiloxanes; mixtures of cyclic- and non-cyclic-modified dimethyl siloxane; and the like. Number average molecular weights are generally about 10,000 or greater. Also suitable are aqueous mixtures of tetraethoxy silane, dimethyl diethoxy silane, and ethylene oxide/dimethyl siloxane copolymer. A preferred composition contains about 5 weight percent tetraethoxy silane, about 5 weight percent dimethyl diethoxy silane, and about 2 weight percent ethylene oxide/dimethyl siloxane copolymer in water. In such silane mixtures, the ethylene oxide-dimethyl siloxane acts as a coupling agent to bind the silicone to the tissue sheet surface, thus retarding residue build-up on the contact surface and thereby reducing the greasy feeling associated with some lubricants.

Surface additive compositions of the foregoing type comprising a silicone compound are disclosed in U.S. Pat. No. 4,950,545 issued Aug. 21, 1990 and U.S. Pat. No. 5,227,242 issued Jul. 13, 1993, both to Walter et al.; the disclosures of which are incorporated herein by reference.

The total amount of silicone solids in the tissue sheet can be from about 0.1 to about 5 weight percent, based on the finished basis weight of the tissue sheet. Preferably the amount of the silicone compound is from about 0.5 to about 3 weight percent and most preferably from about 0.7 to about 2 weight percent. Amounts below 0.1 weight percent alone provide little benefit to the facial tissue in terms of softness improvement. Amounts above 5 weight percent may become economically unattractive.

The primary add-on amount of an additive composition comprising a silicone compound is suitably from about 0.1 to about 5 weight percent, more specifically from about 0.5 to about 3 weight percent, and still more specifically from about 0.7 to about 2 weight percent, based on the weight of the tissue. Moreover, the supplementary add-on amount of an additive composition comprising a silicone compound is suitably from about 0.05 to about 3.5 weight percent, more specifically from about 0.25 to about 1.75 weight percent, and still more specifically from about 0.35 to about 1 weight percent, based on the weight of the tissue. Relative to one another, the supplementary add-on amount for a silicone compound additive composition is preferably from about 0.5 to about 80 percent, more specifically from about 5 to about 70, and still more specifically from about 15 to about 50 percent, of the primary add-on amount.

The presence of the silicone compound additive composition and the differences in add-on amounts in the various zones of the tissue can be verified by infrared spectroscopy and X-ray fluorescence.

The silicone compound can be incorporated into the facial tissue by any suitable means, including printing, spraying, dipping and the like. The silicone compound can be incorporated into the tissue sheet at any point in the tissue manufacturing process. Preferably the silicone compound is printed onto a dried tissue sheet between the base sheet manufacturing process and the final tissue product converting process. Printing provides precise control of the add-on amount of the silicone compound and places the silicone compound on the surface of the tissue in the selected primary and supplementary zones to maximize its effectiveness.

The tissue product of this invention can be one-ply, two-ply, three-ply or more. In all cases, the additive composition is desirably applied to the outer surface(s) of the product. The composition can be applied after the plies are brought together or prior to bringing the plies together. The individual plies can be layered or non-layered (homogeneous).

For purposes herein, "tissue sheet" is a single ply sheet suitable for facial tissue, bath tissue, towels, napkins, or the like having a density of from about 0.04 grams per cubic centimeter to about 0.3 grams per cubic centimeter and a basis weight of from about 4 to about 40 pounds per 2880 square feet. Tensile strengths in the machine direction are in the range of from about 100 to about 5,000 grams per inch of width. Tensile strengths in the cross-machine direction are in the range of from about 50 to about 2500 grams per inch of width. Cellulosic tissue sheets of paper-making fibers are preferred, although synthetic fibers can be present in significant amounts.

DETAILED DESCRIPTION OF THE PREFERRED EMBODIMENTS

Figure 1:
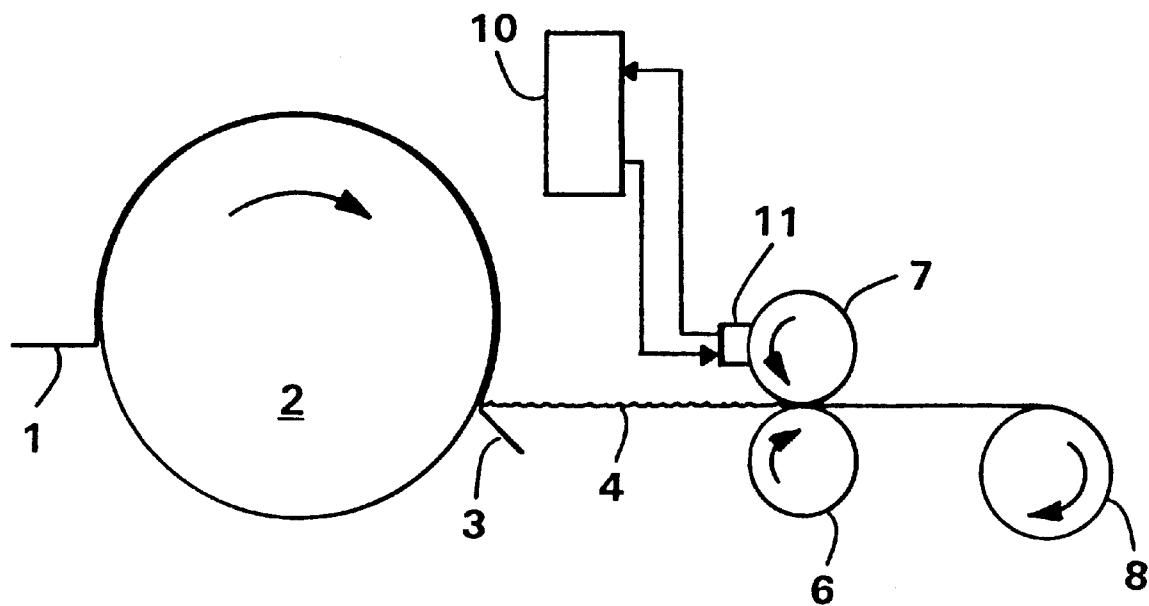
FIG. 1 is a schematic process flow diagram for a method of making a tissue base sheet in which an additive composition is applied to a creped tissue sheet during manufacture using a heated rotogravure printer.

Referring to FIG. 1, a method of carrying out this invention will be described in greater detail. FIG. 1 illustrates a tissue sheet approaching a Yankee dryer 2 and being dislodged from the dryer with a creping blade 3. The dried creped tissue sheet 4 is passed to a heated rotogravure printing station comprising a backing roll 6 and an engraved roll 7, at which point the melted additive composition is applied to one surface of the tissue sheet. The treated tissue sheet is then wound into a roll 8 for subsequent converting operations.

During the printing operation, the melted composition to be applied to the tissue sheet is supplied by a heated supply tank 10 and pumped to a heated doctor application head 11 by a suitable metering pump. It is desirable to maintain constant temperature in the process. Accordingly, the melted composition may be continually circulated between the supply tank and the application head while maintaining an adequate amount in the reservoir. The heated doctor applicator head supplies the melted composition to the engraved roll 7, the surface of which contains a plurality of small cells separated into groups to form the primary and supplementary delivery zones on the final tissue product. As previously noted, the configuration and add-on rates of the primary and supplementary zones are selected to provide the transfer volume necessary to achieve the desired tactile effect. The engraved roll 7 will be discussed in greater detail hereinafter in relation to reference numerals 23A and 23B of FIGS. 7–10.

In operation the engraved roll 7 is loaded to the backing roll 6 to force the tissue web or sheet into contact with the engraved roll. The backing roll can be any material that meets the process requirements such as natural rubber, synthetic rubber or other compressible surfaces. Loading pressures can vary from approximately 5–50 pounds per lineal inch (roll to roll interference) to a gravure roll/backing roll gap of 0.008" (no roll to roll contact).

Figure 2:
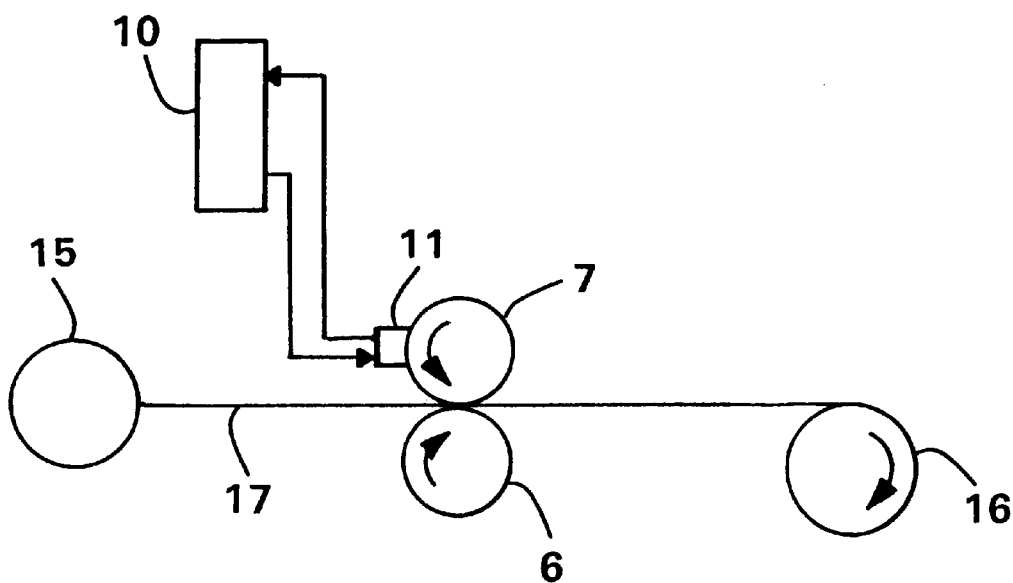
FIG. 2 is a schematic process flow diagram for a method of this invention similar to FIG. 1, in which the web to be treated is sourced from a parent roll.

FIG. 2 is similar to FIG. 1, differing only in that the tissue sheet to be printed with the melted composition is supplied from a parent roll 15. This is intended to depict off-line printing, in which the printing operation is carried out independently of the tissue sheet manufacturing process. The sheet 17 being printed with the melted composition can be a single ply or it can be multiple plies. The resulting sheet is then wound into a roll 16 for further converting operations.

Figure 3:
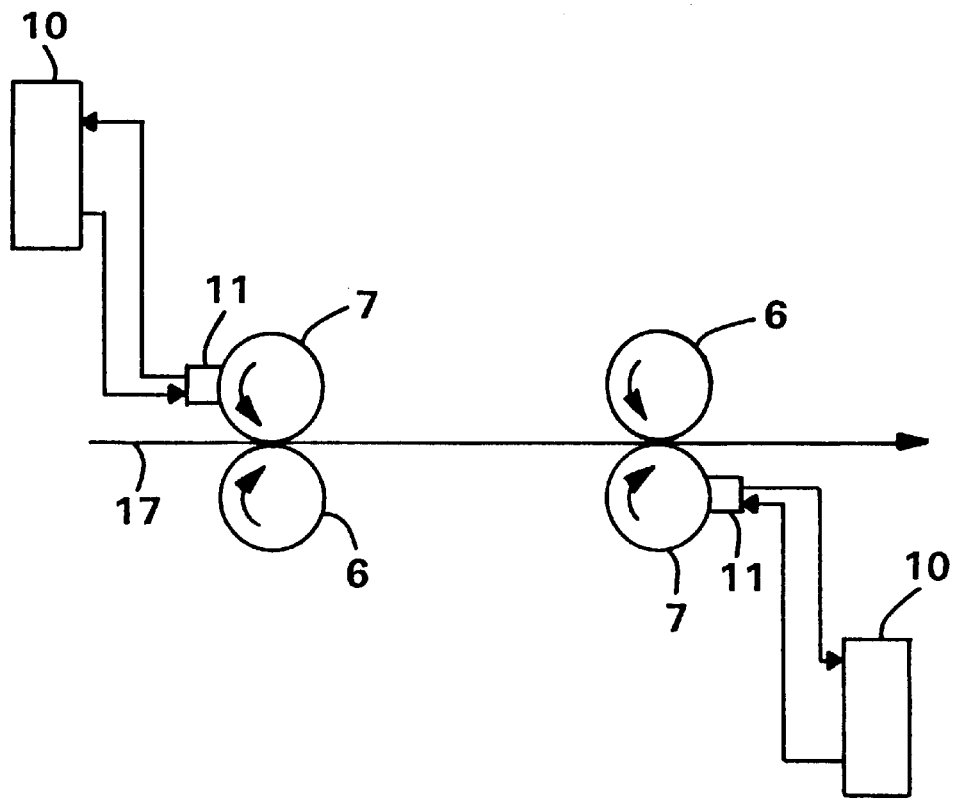
FIG. 3 is a schematic depiction of the heated direct rotogravure process in which the melted composition is applied to both sides of the tissue.

FIG. 3 is similar to FIG. 2, but illustrates two-sided direct heated rotogravure printing of the sheet using two printing stations in sequence. Two-sided printing is desirable when the effect of the composition is desired on both sides and/or the tissue sheet consists of two or more plies.

Figure 4:
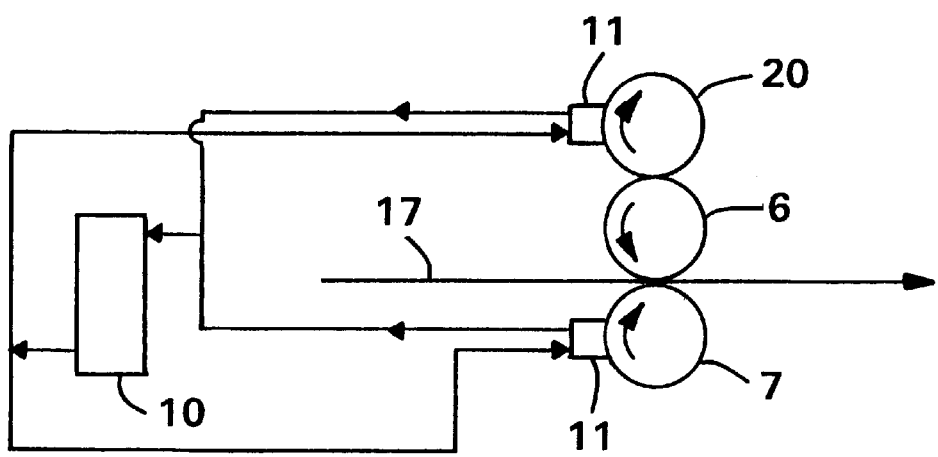
FIG. 4 is a further schematic depiction of a method of this invention in which both sides of the tissue product are printed with the melted composition using a combination of heated offset gravure printing and heated direct gravure printing.

FIG. 4 represents two-sided printing of the tissue sheet using an offset heated gravure printing method on one side of the sheet and a direct heated gravure printing method on the other side of the sheet. In this method, the engraved roll 7 and the backup roll 6 (now doubling as an offset applicator roll) can be the same as the rolls used for the previously described methods. However, a second engraved roll 20 requires different liquid delivery characteristics and thus is engraved slightly differently. For such rolls, for example, the direct engraving specifications for the primary delivery zones can be 200 line screen, 5.0 BCM. Typical cell dimensions for such a roll can be 150 microns in length, 110 microns in width, and 30 microns in depth. The offset engraving specifications for the primary delivery zones can be 250 line screen, 4.0 BCM, 140 microns in length, 110 microns in width, and 26 microns in depth. The engraving specifications for the supplementary delivery zones can be adapted to provide relatively lower add-on amounts.

Figure 5:
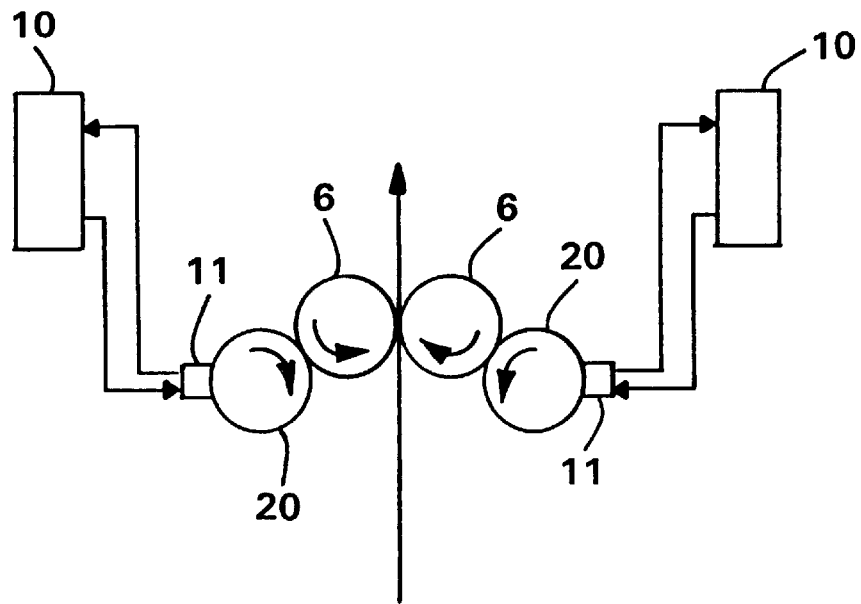
FIG. 5 is a further schematic depiction of a method of this invention in which both sides of a tissue are simultaneously printed with the melted composition using heated offset gravure printing.

FIG. 5 represents a method of printing both sides of the sheet using simultaneous heated offset gravure printing.

Figure 6:
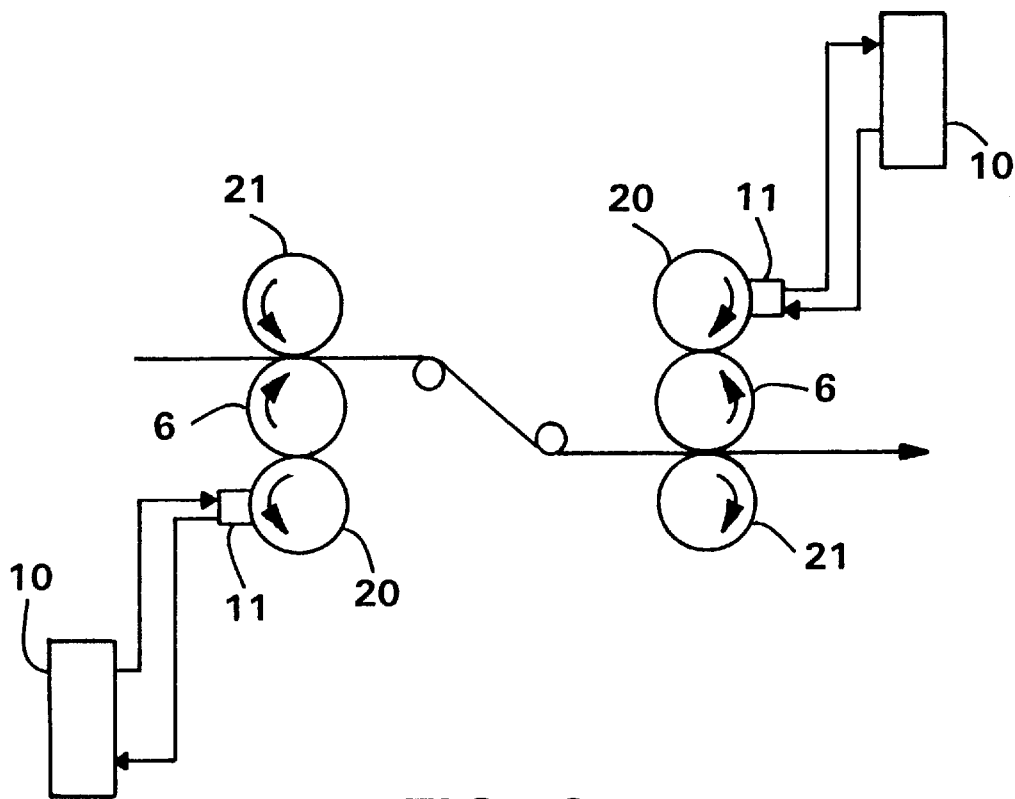
FIG. 6 is a further schematic depiction of a method of this invention in which both sides of the tissue sheet are consecutively printed with the melted composition using heated offset gravure printing.

FIG. 6 represents a method of printing both sides of the sheet in succession using two heated offset gravure printing stations. For each printing station, the addition of a backing roll 21 is necessary.

Figure 7:
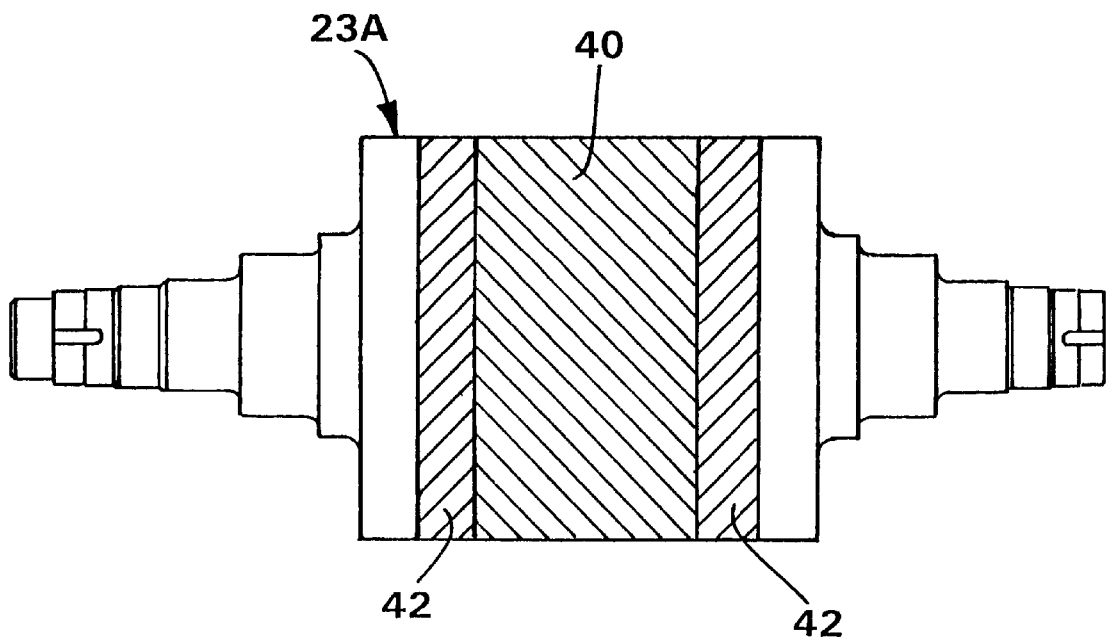
FIG. 7 representatively shows a top plan view of one exemplary engraved roll for use in manufacturing tissue products.

One exemplary engraved roll 23A suitable for use in applying additives to facial tissue in zones of differing add-on amounts is shown in FIG. 7. The engraved roll is engraved with two different regions of cell patterns. A primary region 40 has a line screen of 200 cells per lineal inch. Each cell has a volume of 5.0 billion cubic microns (BCM) per square inch of roll surface, with typical dimensions of 180 microns in length, 143 microns in width, and 30 microns in depth. The resulting additive deposits are approximately 2.2 gsm. The primary region 40 is laterally surrounded by a pair of supplementary regions 42. The supplementary regions 42 each have a line screen of 390 cells per lineal inch. The cells in the supplementary regions 42 have a volume of 1.5 BCM per square inch of roll surface, and typical dimensions of 110 microns in length, 65 microns in width, and 18 microns in depth. The additive deposits resulting from the supplementary regions 42 are approximately 0.42 gsm.

The combined regions 40 and 42 represent the print coverage width of facial tissue, approximately 8.5 inches. The primary region 40 is positioned in the center 5.5 inches of the tissue and covers approximately 65 percent of the planar surface area of the tissue. The supplementary regions 42 are each 1.5 inches in width and cumulatively cover approximately 35 percent of the planar surface area.

Figure 8:
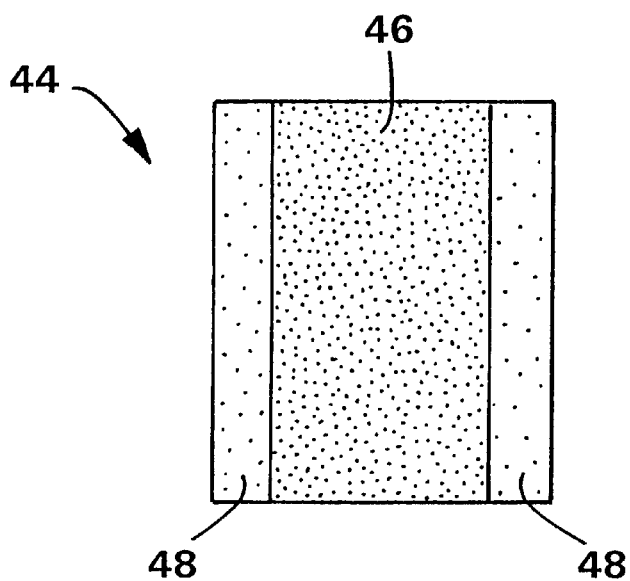
FIG. 8 representatively shows a tissue product manufactured using the engraved roll of FIG. 7 and treated with osmiun tetroxide to stain the additive composition black.
Figure 10:
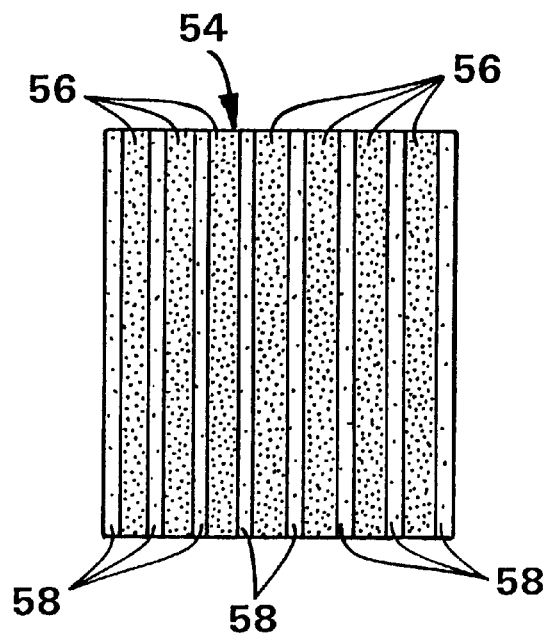
FIG. 10 representatively shows a tissue product manufactured using the engraved roll of FIG. 9 and treated with osmiun tetroxide to stain the additive composition black.

FIG. 8 representatively shows a facial tissue 44 that would result from using the engraved roll 23A of FIG. 7. The tissue 44 is illustrated as having been treated with osmiun tetroxide to stain the additive composition black. The result of the treatment shows a central primary delivery zone 46 that is a darker shade than a pair of laterally spaced supplementary delivery zones 48. In FIGS. 8 and 10 darker shading is illustrated by more closely spaced speckle marks. The darker shade indicates the presence of more additive in the primary delivery zone 46 than in the supplementary delivery zones 48. The primary delivery zone 46 is centrally located to maximize the opportunity for additive to contact the skin of the user. The supplementary delivery zones 48 are uniformly coated with the same additive that is present in the primary delivery zone, but at a reduced amount. This allows the supplementary delivery zones to provide some benefit, but most importantly does not drastically detract from the benefit delivered by the primary delivery zone. In one embodiment, the tissue 44 does not include additive void areas, for it is hypothesized that such void areas when used as an alternative to supplementary delivery zones significantly diminish the effectiveness of the primary delivery zone.

Figure 9:
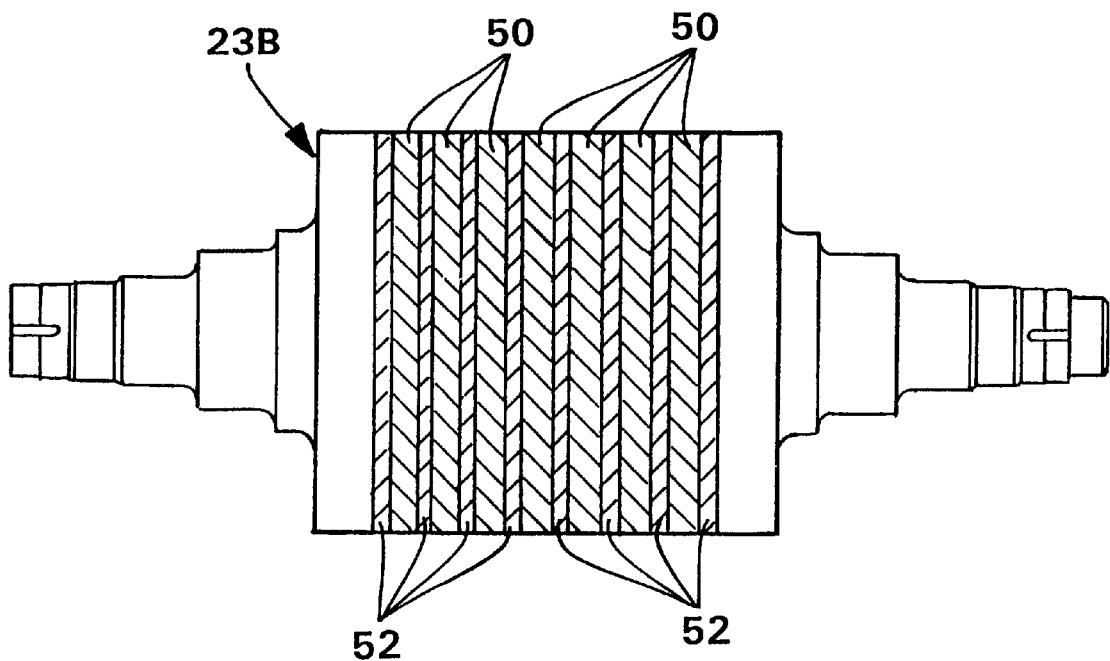
FIG. 9 representatively shows a top plan view of another exemplary engraved roll for use in manufacturing tissue products.

FIG. 9 shows another exemplary engraved roll 23B suitable for use in applying additives to facial tissue in zones of differing transfer. The engraved roll includes an alternating pattern of two different regions of cell patterns. A plurality of primary regions 50 deliver additive deposits at approximately 2.2 gsm, and a plurality of supplementary regions 52 deliver additive deposits at approximately 0.42 gsm. These regions 50 and 52, have the same line screen, cell volume, and dimensions, respectively, as those described above in relation to the primary and secondary regions 40 and 42 of FIG. 7.

The combined regions 50 and 52 in FIG. 9 have a print coverage width of approximately 8.5 inches. The seven primary regions 50 are each approximately 0.75 inch wide, and cumulatively cover approximately 62 percent of the planar surface area of the tissue. The eight supplementary regions 52 are each 0.41 inch wide and cumulatively cover approximately 38 percent of the planar surface area.

FIG. 10 representatively shows a facial tissue 54 that would result from using the engraved roll 23B of FIG. 9. The tissue 54 is illustrated as having been treated with osmiun tetroxide. The tissue includes seven distinct primary delivery zones 56 that appear darker than eight supplementary delivery zones 58. The primary delivery zones tend to mask the reduced amount of additive in the supplementary delivery zones. The placement of the supplementary delivery zones adjacent and laterally outward from the primary delivery zones maintains the benefits resulting from the primary delivery zones.

Although FIGS. 7 and 9 both show striped zones that are continuous in one direction, it is possible to obtain changes in the additive application rate using different methods. For example, a block, circle, or other shaped zone could be introduced to repeat at specified intervals.

EXAMPLE

The following example serves to illustrate possible approaches pertaining to the present invention. The particular amounts, proportions, compositions and parameters are meant to be exemplary, and are not intended to specifically limit the scope of the invention.

A skin-moisturizing formula was prepared having the following composition:

|  | Weight Percent |
|---|---|
| 1. Dimethicone 100 cst | 1.0 |
| 2. Isopropyl Palmitate | 3.0 |
| 3. Vitamin E Acetate | 0.1 |
| 4. Aloe Extract | 0.1 |
| 5. Mineral Oil | 59.8 |
| 6. Ceresin Wax (M.P. 66–71° C.) | 18.0 |
| 7. Cetearyl Alcohol | 18.0 |

The formulation was prepared by premixing the dimethicone and the isopropyl palmitate until uniform. While heating, the aloe vera extract and the vitamin E extract were added and mixed. Mineral oil was added and the formulation was mixed until uniform. The mixture was further heated to a temperature of 55–60° C. The ceresin wax was added. The mixture was further heated to 60–65° C. with agitation until the ceresin wax was melted. Cetearyl alcohol was slowly added to the mixture while maintaining agitation to avoid clumping. The temperature was maintained at about 55–60° C. and mixing continued until the cetearyl alcohol was melted. At this point the formulation was ready for use.

The resulting formulation was applied to both surfaces of a wet-pressed three-ply tissue basesheet (basis weight of about 23 pounds per 2880 square feet) via a simultaneous heated rotogravure printing process at an add-on level of 6.8 weight percent total add-on as described in relation to FIG. 5. Specifically, the formulation was pre-melted at about 56° C. in a stainless steel heated supply tank. The press supply system and press (supply hoses, doctor application heads, and gravure rolls) were preheated to about 55° C. The formulation was transferred from the heated application heads to the heated offset/offset gravure rolls.

The gravure rolls were electronically engraved, chrome over copper rolls supplied by Southern Graphics Systems, Louisville, Kentucky. Each heated gravure roll included two different cell patterns as illustrated in FIG. 8. A centrally-located primary region had a line screen of 200 cells per lineal inch and a volume of 5.0 BCM per square inch of roll surface. Typical cell dimensions for this roll were 180 microns in length, 143 microns in width, and 30 microns in depth. This primary region was laterally surrounded by a pair of supplementary regions, each having a line screen of 390 cells per lineal inch and a volume of 1.5 BCM per square inch of roll surface. Typical cell dimensions for this roll were 110 microns in length, 65 microns in width, and 18 microns in depth. The stylus angle was set at 135 degrees for the primary region and 145 degrees for the supplementary regions. The rubber backing offset applicator rolls were a 75 Shore A durometer cast polyurethane supplied by American Roller Company, Union Grove, Wis.

The process was set up to a condition having 0.375 inch interference between the gravure rolls and the rubber backing rolls, and 0.003 inch clearance between the facing rubber backing rolls. The simultaneous offset/offset heated gravure printer was run at a speed of 2000 feet per minute. The composition deposits solidified substantially instantaneously after exiting the press.

When cut into individual facial tissue sheets, the resulting tissue product was directionally preferred by consumers for overall performance over comparable facial tissues having a generally uniform additive application at an add-on level of 10.4 weight percent total add-on. The tissues incorporating the primary and supplementary delivery zones also provide a significant cost advantage of the uniform additive application tissues, due to the multiple add-on level tissues including 35 percent less additive.

It will be appreciated that the foregoing example, given for purposes of illustration, is not to be construed as limiting the scope of this invention, which is defined by the following claims and all equivalents thereto.

We claim:

1. A tissue product defining a major surface having a planar surface area, the tissue product comprising an additive composition disposed on the major surface in at least one primary delivery zone having a primary add-on level and at least one supplementary delivery zone having a supplementary add-on level, the supplementary add-on level being greater than zero and from about 0.5 to about 80 percent of the primary add-on level.

2. A tissue product defining a major surface having a planar surface area, the tissue product comprising an additive composition disposed on the major surface in at least one primary delivery zone having a primary add-on level and at least one supplementary delivery zone having a supplementary add-on level, the supplementary add-on level being greater than zero and the primary add-on level being greater than the supplementary add-on level, the primary delivery zone covering from about 30 to about 90 percent of the planar surface area and the supplementary delivery zone covering from about 10 to about 70 percent of the planar surface area.

3. The tissue product of claim 2, wherein the supplementary add-on level is from about 0.5 to about 80 percent of the primary add-on level.

4. The tissue product of claim 1 or 2, wherein the supplementary add-on level is from about 5 to about 70 percent of the primary add-on level.

5. The tissue product of claim 4, wherein the supplementary add-on level is from about 15 to about 50 percent of the primary add-on level.

6. The tissue product of claim 1, wherein the primary and supplementary delivery zones each comprise from about 100 to about 1,000,000 individual deposits per square inch of the planar surface area.

7. The tissue product of claim 1 or 2, wherein the primary delivery zone covers from about 40 to about 80 percent of the planar surface area and the supplementary delivery zone covers from about 20 to about 60 percent of the planar surface area.

8. The tissue product of claim 7, wherein the primary delivery zone covers from about 50 to about 75 percent of the planar surface area and the supplementary delivery zone covers from about 25 to about 50 percent of the planar surface area.

9. The tissue product of claim 1 or 2, wherein the primary and supplementary delivery zones have a combined surface area of at least about 75 percent of the planar surface area.

10. The tissue product of claim 9, wherein the primary and supplementary delivery zones have a combined surface area of at least about 88 percent of the planar surface area.

11. The tissue product of claim 9, wherein the primary and supplementary delivery zones have a combined surface area of 100 percent of the planar surface area.

12. The tissue product of claim 1 or 2, wherein the primary delivery zone has a width dimension of from about 0.2 to about 4 inches and the supplementary delivery zone has a width dimension of from about 0.1 to about 2 inches.

13. The tissue product of claim 12, wherein the primary delivery zone has a width dimension of from about 0.4 to about 2 inches and the supplementary delivery zone has a width dimension of from about 0.2 to about 1 inch.

14. The tissue product of claim 12, wherein the primary delivery zone has a width dimension of from about 0.5 to about 1.5 inch and the supplementary delivery zone has a width dimension of from about 0.25 to about 0.75 inch.

15. The tissue product of claim 1 or 2, wherein the primary delivery zone is laterally surrounded by the supplementary delivery zone.

16. The tissue product of claim 1 or 2, wherein the primary delivery zone is positioned immediately adjacent the supplementary delivery zone.

17. The tissue product of claim 1 or 2, wherein the primary delivery zone comprises a plurality of primary delivery zones and the supplementary delivery zone comprises a plurality of supplementary zones.

18. The tissue product of claim 1 or 2, wherein the additive composition within each primary and supplementary delivery zone comprises from about 30 to about 90 weight percent oil and from about 10 to about 40 weight percent wax, said composition having a melting point of from about 30° C. to about 70° C.

19. The tissue product of claim 18, wherein the primary add-on level is from about 3 to about 15 weight percent and the supplementary add-on level is from about 0.5 to about 12 weight percent.

20. The tissue product of claim 18, wherein the primary add-on level is from about 4 to about 10 weight percent and the supplementary add-on level is from about 1 to about 8 weight percent.

21. The tissue product of claim 18, further comprising from about 5 to about 40 weight percent fatty alcohol.

22. The tissue product of claim 18, wherein the amount of oil in the composition is from about 40 to about 70 weight percent.

23. The tissue product of claim 18, wherein the amount of wax in the composition is from about 10 to about 30 weight percent.

24. The tissue product of claim 1 or 2, wherein the additive composition within each primary and supplementary delivery zone comprises a silicone compound.

25. The tissue product of claim 24, wherein the primary add-on level is from about 0.5 to about 3 weight percent and the supplementary add-on level is from about 0.25 to about 1.75 weight percent.

26. The tissue product of claim 24, wherein the primary add-on level is from about 0.7 to about 2 weight percent and the supplementary add-on level is from about 0.35 to about 1 weight percent.

27. The tissue product of claim 1, wherein the primary and supplementary delivery zones comprise different additive compositions.

28. A method of making a tissue product comprising:
providing a tissue web and an additive composition;
applying the additive composition to the tissue web using a rotogravure process comprising an engraved roll having primary and supplementary regions, the primary and supplementary regions adapted to provide different add-on rates; and
recovering from the rotogravure process a tissue product having the additive composition disposed in both a primary delivery zone having a primary add-on level and a supplementary delivery zone having a supplementary add-on level, the supplementary add-on level being greater than zero and from about 0.5 to about 80 percent of the primary add-on level.

29. The method of claim 28, wherein the primary region of the engraved roll comprises cells having a cell volume of about 0.5 to about 15 cubic billion microns per square inch, and the supplementary region of the engraved roll comprises cells having a lesser cell volume of about 0.1 to about 10 cubic billion microns per square inch.

30. The method of claim 28, wherein the primary region of the engraved roll comprises cells having a cell volume of about 1 to about 10 cubic billion microns per square inch, and the supplementary region of the engraved roll comprises cells having a lesser cell volume of about 0.5 to about 8 cubic billion microns per square inch.

31. The method of claim 28, wherein the primary region of the engraved roll comprises cells having a cell volume of about 1.5 to about 8 cubic billion microns per square inch, and the supplementary region of the engraved roll comprises cells having a lesser cell volume of about 0.75 to about 6 cubic billion microns per square inch.

* * * * *